US006645144B1

United States Patent
Wen et al.

(10) Patent No.: US 6,645,144 B1
(45) Date of Patent: Nov. 11, 2003

(54) ELECTROACOUSTIC IMAGING METHODS AND APPARATUS

(75) Inventors: Han Wen, Gaithersburg, MD (US); Robert S. Balaban, Bethesda, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 09/807,730

(22) PCT Filed: Oct. 12, 1999

(86) PCT No.: PCT/US99/21610

§ 371 (c)(1),
(2), (4) Date: May 18, 2001

(87) PCT Pub. No.: WO00/22987

PCT Pub. Date: Apr. 27, 2000

Related U.S. Application Data (60) Provisional application No. 60/104,823, filed on Oct. 19, 1998.

(51) Int. Cl.[7] ................................................. A61B 8/00
(52) U.S. Cl. ...................................... 600/437; 600/407
(58) Field of Search ................................ 600/407–412; 73/643, 597–602

(56) References Cited

U.S. PATENT DOCUMENTS

| | | | |
|---|---|---|---|
| 3,946,600 A | | 3/1976 | Rettig et al. |
| 4,385,634 A | * | 5/1983 | Bowen ....................... 600/407 |
| 4,497,208 A | | 2/1985 | Oja et al. |
| 4,523,473 A | * | 6/1985 | Chamuel ..................... 73/216 |
| 4,543,959 A | * | 10/1985 | Sepponen ................... 324/309 |
| 4,745,809 A | | 5/1988 | Collins et al. |
| 4,821,731 A | * | 4/1989 | Martinelli et al. .......... 600/439 |
| 5,170,666 A | | 12/1992 | Larsen |
| 5,495,175 A | | 2/1996 | Ramirez et al. |
| 5,553,610 A | | 9/1996 | Lodder |
| 5,713,356 A | * | 2/1998 | Kruger ....................... 600/407 |
| 5,924,986 A | * | 7/1999 | Chandler et al. ........... 600/407 |
| 6,104,942 A | * | 8/2000 | Kruger ....................... 600/407 |
| 6,159,154 A | * | 12/2000 | Takeuchi .................... 600/458 |

FOREIGN PATENT DOCUMENTS

| | | |
|---|---|---|
| WO | WO 98/00732 | 1/1998 |
| WO | WO 98/19138 | 5/1998 |

OTHER PUBLICATIONS

Roth, Bradley J., Basser, Peter J., and Wikswo, Jr., John P., A Theoretical Model for Magneto–Acoustic Imaging of Bioelectric Currents, IEEE Transactions on Biomedical Engineering, vol. 41, No. 8, Aug. 1994, p. 723–728.*

Roth, Bradley J., Basser, Peter J., and Wikswo, Jr., John P., A Theoretical Model for Magneto–Acoustic Imaging of Bioelectric Currents, IEEE Transactions on Biomedical Engineering, vol. 41, No. 8, Aug. 1994, p. 723–728.*

Beck et al., "Measuring Zeta Potential by Ultrasonic Waves: a New Method," *Tappi* 61:63–65 (Sep. 1978).

Borsay and Yeager, "Generation of ultrasound at metal–electrolyte interfaces," *J. Acoust. Soc. Am.* 64:240–242 (Jul. 1978).

(List continued on next page.)

*Primary Examiner*—Marvin M. Lateef
*Assistant Examiner*—William Jung
(74) *Attorney, Agent, or Firm*—Klarquist Sparkman LLP (57) ABSTRACT

Methods are disclosed for obtaining electroacoustic images of specimens. One method includes applying an acoustic wave to a specimen and forming an image based on an electroacoustically induced electric field or voltage. In another method, an electric field or voltage is applied to a specimen and an electroacoustically induced acoustic wave is measured to form an image. Apparatus suitable for obtaining electroacoustc images are disclosed as well as methods for distinguishing image contributions from the electroacoustic, thermoacoustic, and Hall effects.

23 Claims, 7 Drawing Sheets

OTHER PUBLICATIONS

Bugosh et al., "The Application of Ultrasonic Waves to the Study of Electrolytic Solutions," *J. Chem. Phys.* 15:592–597, (Aug. 1947).

Cannon, David. W., "New Developments in Electroacoustic Methods and Instrumentation," *NIST Special Publication No. 856*, 1993, pp. 40–65.

Debye, P., "A Method for the Determination of the Mass of Electrolytic Ions," *J. Chem. Phys.* 1:13–16.

Döler, W., "Grundlagenuntersuchungen zur Impediographie," *Ultraschall* 6:152–155, (1985).

Dukhin and Goetz, "Acoustic and Electroacoustic Spectroscopy," *Langmuir* 12:4336 (1996).

Dukhin, S.S., "Development of Notions as to the Mechanism of Electrokinetic Phenomena and the Structure of the Colloid Micelle," in Surface and Colloid Science, vol. 7, E. Matijevic, ed., Wiley (1974).

Goetz and El–Aasser, "Effects of Dispersion Concentration on the Electroacoustic Potentials of o/w Miniemulsions," *J. Colloid Interface Sci.* 150:436–452 (May 1992).

Malmivao and Plonsey, "Impedance Tomography," in Bio-electromagnetism, Oxford, 1995.

O'Brian, R.W., "Electro–acoustic effects in a dilute suspension of spherical particles," *J. Fluid Mech.* 190:71–86 (1988).

Scales and Jones, "Effect of Particle Size Distribution on the Accuracy of Electroacoustic Mobilities," *Langmuir* 8:385–389 (1992).

Splitt, G., "Ultrasonic Probes for Special Tasks—the Optimum Probe for each Application," Krautkkrämer GmbH & Co., Hürth, Germany (undated).

Tankovsky, N.S., "Electromagnetic excitation of ultrasound in electrolytes," *Appl. Phys. Lett.*, 69:3327–3329 (Nov. 1996).

Tankovsky, N., "Electroacoustic effect in electrolytes," *J. Appl. Phys.* 75:1239–1241 (Jan. 1994).

Tankovsky and Burov, "Sound Generation in Liquids by Electrically Driven Ions in Dilute Electrolytes," *J. Phys. Chem.* 98:10930–10934 (1994).

Yeager et al., "The Application of Ultrasonic Waves to the Study of Electrolytic Solutions," *J. Chem. Phys.* 17:411–415 (Apr. 1949).

\* cited by examiner

ELECTROACOUSTIC IMAGING METHODS AND APPARATUS

This application claims the benefit of provisional application Ser. No. 60/104,823 filed Oct. 19, 1998.

FIELD OF THE INVENTION

The invention pertains to acoustic imaging methods and apparatus.

BACKGROUND OF THE INVENTION

Conventional ultrasound imaging produces images that reveal spatial variations in the acoustic impedance of a specimen. In particular, conventional ultrasound images reveal the structure of the specimen based on either the absorption of acoustic waves by the specimen or reflection of acoustic waves in the specimen. The measured reflectances result from abrupt changes in the acoustic impedance of the specimen at material interfaces within the specimen. As one example, in clinical imaging of a human fetus an image of the fetus is obtained based on the difference in acoustic impedance of the fetus and the surrounding amniotic fluid as well as acoustic impedance differences within the fetus.

Because many materials transmit acoustic waves conventional ultrasound imaging provides a method of observing the interior of a variety of specimens, including metallurgical and biological samples. Unfortunately, the conventional ultrasound image depends solely on the acoustic impedance of the specimen and many specimens of interest have a nearly constant acoustic impedance. Thus, the conventional ultrasound images of these specimens lack contrast and reveal little of the specimen's structure.

Imaging methods have also been described that use an acoustic wave in combination with a specimen property other than the acoustic impedance. For example, thermoacoustic imaging uses optical or microwave radiation to produce localized heating in a specimen. The localized heating depends on the local absorption of the incident radiation and the specimen heat capacity. The localized heating causes a corresponding localized thermal expansion of the specimen that produces an acoustic wave. Images obtained in this way reveal spatial variations in specimen absorptivity, heat capacity, and thermoelastic properties of the specimen.

In another imaging method, a specimen is situated in a magnetic field and an acoustic wave is applied to generate a Hall voltage. The Hall voltage is detected and processed to form an image that reveals localized spatial variations in specimen conductivity. In a variation of this method, an electric field is applied to the specimen, generating an acoustic wave caused by charge movement produced by the Hall effect. The acoustic wave is detected and processed to form an image that depends on the local conductivity.

These methods can provide useful specimen images, but for some specimens, the images have low contrast or fail to reveal important specimen features. In addition, the images produced by these methods may not correspond to specimen properties of interest. For example, conventional ultrasound images of biological specimens primarily reveal density variations in the specimen. While these density variations often produce acceptable images, in many cases specimen properties other than density are important. For example, conventional ultrasound does not reveal specimen ionic properties such as conductivity and mobility, does not distinguish electrolytes from non-electrolytes, and does not distinguish extensively cross-linked materials from more loosely bound materials. Accordingly, improved imaging techniques are needed.

SUMMARY OF THE INVENTION

Methods and apparatus for forming images of a specimen based on the electroacoustic properties of the specimen are provided. In addition, methods and apparatus for distinguishing Hall, thermoacoustic, and electroacoustic images are provided.

In an embodiment, an electroacoustic image of a specimen is obtained by applying a probe signal, such as either an acoustic wave or an electric field (or voltage), to the specimen. The probe signal produces an induced signal that is a function of an electroacoustic parameter of the specimen. If the probe signal is an acoustic wave, then the induced signal is an electric field or voltage. If the probe signal is an electric field or voltage, then the induced signal is an acoustic wave. The induced signal is detected and an image is generated based on the detected induced signal.

In one embodiment, the probe signal is an acoustic wave that propagates along an axis of propagation. The electric field is then detected along an axis that is substantially parallel to the axis of propagation. In another embodiment, the electric field is applied parallel to an axis and the acoustic wave is detected in a direction parallel to the axis. These embodiments take advantage of the directional properties of the probe signal and the induced signal.

In some embodiments, a magnetic field is also applied to the specimen. The induced signal is then a function of the applied magnetic field and the image includes an electroacoustic contribution and a Hall effect contribution. Either an acoustic wave or an electric field is applied as the probe signal and produces an induced electric field or acoustic wave, respectively.

In a further embodiment, the probe signal is applied along a plurality of incrementally moved, substantially parallel axes to obtain a two-dimensional image or a three dimensional image of the specimen.

In still another embodiment, a purely electroacoustic image and a purely Hall effect image can be obtained. A first magnetic field is applied to a specimen to obtain a first image of the specimen. The first image then includes both electroacoustic effect and Hall effect contributions. A second magnetic field is then applied in a direction opposite to the direction of the first magnetic and a second image of the specimen is obtained. The second image also includes electroacoustic and Hall effect contributions. A purely electroacoustic image is then obtained by combining the first and second images to substantially eliminate the Hall effect contribution. In addition, the first and second images can be combined in such a way to obtain a purely Hall effect image.

In additional embodiments, thermoacoustic contributions to images can be distinguished. In one method, a first voltage having a first polarity is applied to a specimen to obtain a first image. A second voltage of polarity opposite that of the first voltage is then applied to the specimen to obtain a second image. The first and second images are then combined to obtain a purely electroacoustic image. In addition, the first and second images can be combined to obtain a purely thermoacoustic image.

An apparatus for electroacoustic imaging of a specimen is disclosed that includes an acoustic transducer that produces an acoustic wave in the specimen. The acoustic wave electroacoustically generates an electric field that is detected with electrodes that generate a voltage in response to the electric field. An image processor receives the voltage from the electrodes and produces an image of the specimen on a display. In an embodiment, the acoustic wave has a duration of less than about 1000 ns.

In a further embodiment, an apparatus for forward or reverse electroacoustic imaging of a specimen includes an acoustic transducer situated to transmit an acoustic wave to the specimen or to receive an acoustic wave from the specimen. Two or more electrodes are positioned to apply a voltage to the specimen to electroacoustically generate an acoustic wave or to detect an electroacoustically generated voltage produced by the acoustic wave transmitted by the acoustic transducer. An image processor receives the electroacoustically generated voltage or acoustic wave and forms an image of the specimen.

The disclosed imaging methods and apparatus are suitable for imaging a variety of specimens including, for example, biological specimens, animal tissues, and human bodies, including tumors or human bodily organs, such as the human heart. The methods and apparatus are applicable to both in vivo and in vitro imaging.

Other features and advantages of the invention will be apparent from the following detailed description and figures.

DETAILED DESCRIPTION

The generation of an electric field by application of an acoustic wave to an electrolyte or a colloidal suspension is referred to herein as the electroacoustic effect. An applied acoustic wave produces a separation of positive and negative charges, generating an electric field that can be measured as a voltage. The electroacoustic effect also includes the generation of an acoustic (sound) wave by the application of an electric field. An applied electric field causes opposite charges in the electrolyte or colloidal suspension to move in opposite directions and at speeds dependent on the mobilities of the charges. This motion generates an acoustic wave.

The electroacoustic generation of a voltage by the application of an acoustic wave to a specimen is referred to herein as the "forward" electroacoustic effect. The electroacoustic generation of an acoustic wave by the application of an electric field is referred to herein as the "reverse" electroacoustic effect. The forward and reverse electroacoustic effects are closely related and satisfy a known reciprocity relation so that a measurement of a specimen using one of these effects measures the same quantity as the other effect.

Electroacoustic imaging methods and apparatus are disclosed in which a sample is imaged by (a) applying an acoustic wave to produce an electric field that is then detected to form an image, or (b) applying an electric field to produce an acoustic wave that is then detected to form an image. Method (a) is referred to as "forward" electroacoustic imaging and method (b) as "reverse" electroacoustic imaging. The images obtained by either method (a) or (b) display the local electroacoustic properties of the sample. There can be, however, practical reasons for selecting a particular effect (i.e., forward or reverse).

Forward and reverse electroacoustic imaging can be generally described as the application of a probe signal and the detection and measurement of an induced signal. In forward electroacoustic imaging, the probe signal is an acoustic wave and the induced signal is an electric field (or voltage); in reverse electroacoustic imaging, the probe signal is an electric field (or voltage) and the induced signal is an acoustic wave.

The extent to which an applied electric field produces an acoustic wave electroacoustically depends on a material constant referred to herein as the electroacoustic parameter $C_{ea}$. In general, the electroacoustic parameter $C_{ea}$ of a specimen varies throughout the specimen and can be expressed as $C_{ea}(r)$, where r is a coordinate representing a location within the specimen. Variations in $C_{ea}(r)$ are displayed in images based on this parameter. The extent to which an applied acoustic wave induces an electric field also depends on the electroacoustic parameter $C_{ea}(r)$.

One phenomenological model of the relationship of the electroacoustic parameter $C_{ea}$ to material parameters is given by:

$$C_{ea} = \frac{\sum_j n_j q_j m_j / \eta_j}{1 - i\frac{2\sigma}{\varepsilon f}}$$

where $n_j$, $q_j$, $m_j$, $\eta_j$ are the number density, charge, mass, and friction constant of the jth ionic species, $\sigma$ and $\varepsilon$ are the conductivity and dielectric constant of the electrolyte, $f$ is the frequency of the applied electric field, i is the square root of negative one, and the summation is over all ionic species in the electrolyte. This expression shows that $C_{ea}$ depends on the mass to friction ratio $m/\eta$ of the ionic species so that large ions (large masses m) tend to be associated with large values of $C_{ea}$. Similarly, large values of $C_{ea}$ are associated with small values of the friction constant $\eta$. The ratio $m/\eta$ determines how readily the ion follows the movement of the solvent.

For colloidal suspensions, the electroacoustic effect has been theoretically studied by O'Brien (R. W. O'Brien, "Electro-acoustic Effects in a Dilute Suspension of Spherical Particles," J. Fluid Mechanics, vol. 190, pp. 71–86, 1988) and Dubkin and Goetz (A. S. Dukhin and P. J. Goetz, "Acoustic and Electroacoustic Spectroscopy," Langmuir, vol. 10, pp. 4336–4344, 1996). A double layer theory for $C_{ea}$ has been developed in which a colloidal particle is modeled as a rigid core covered by a thin fluid layer, wherein the interior and exterior of the thin fluid layer carry opposite charges. When a high frequency acoustic wave is applied, the thin fluid layer slides and compresses differentially around the core, redistributing the charge carried on the interior and exterior surfaces. In this model, $C_{ea}$ depends on the size of the particle, the nature of the particle surface layer, and the total potential difference across the surface layer (the so-called ζ-potential). This model has been used successfully with a variety of suspensions, including milk and silica emulsions.

In some specimens of interest, the conductivity, acoustic impedance, or thermoelastic properties are relatively constant throughout the specimen. For example, muscle and blood have similar acoustic and electrical properties but different macromolecular contents and different degrees of interconnectivity. Images of specimens containing muscle and blood (and muscle/blood interfaces) based on the electroacoustic parameter $C_{ea}(r)$ are superior to images obtained with conventional ultrasound, Hall effect, or thermoacoustic effect imaging methods. One important clinical application of electroacoustic imaging is in vivo imaging of blood perfusion through the heart or skeletal muscles. Another important application of electroacoustic imaging is the detection and classification of tumors. The cells of tumors undergo structural changes that disorganize their membrane structures, leading to changes in the electroacoustic parameter $C_{ea}(r)$ of the tumor. Late stage tumors tend to exhibit little macromolecular structure in comparison with the initial stage so that electroacoustic imaging of the tumor facilitates tumor classification (for example, as late or early stage) and permits the physician to select an appropriate treatment.

For specimens in which other methods produce satisfactory images, images based on the electroacoustic parameter $C_{ea}$ provide additional specimen details. Specimens of interest therefore include biological specimens and living organisms, tumors, and bodily organs such as the heart and lungs of humans and other animals.

As used herein, an image of a specimen consists of an array of values associated with locations in a specimen. The values can be positive or negative, and can be expressed as real or imaginary numbers, or as a magnitude and a phase. The values correspond to a local property of the specimen. An image can be represented, for example, as a time varying electrical voltage such as a video signal, or can be stored in a computer readable medium such as a disk or magnetic tape. A variety of storage formats are known, some of which transform the image values before storage to reduce storage requirements in the computer readable medium.

The electric field applied to the specimen or induced in the specimen by the acoustic wave propagates at the speed of light in the specimen and is therefore incident on electrodes that detect the electric field almost simultaneously from all portions of the specimen. In conventional acoustic imaging both the applied acoustic wave and the received acoustic wave propagate at a sound velocity, typically 1400–1500 m/sec and a received sound signal is located by measuring the elapsed time from the initiation of the probe acoustic wave to determine an approximate location. In electroacoustic imaging, the elapsed time from the application of a voltage to detection of an acoustic wave (reverse electroacoustic imaging) or the elapsed time from the transmission of an acoustic wave to detection of an induced voltage (forward electroacoustic effect) are conveniently measured because the propagation of the applied voltage to the specimen or the induced voltage from the specimen depends on the speed of light in the specimen and is very fast.

Figure 1:
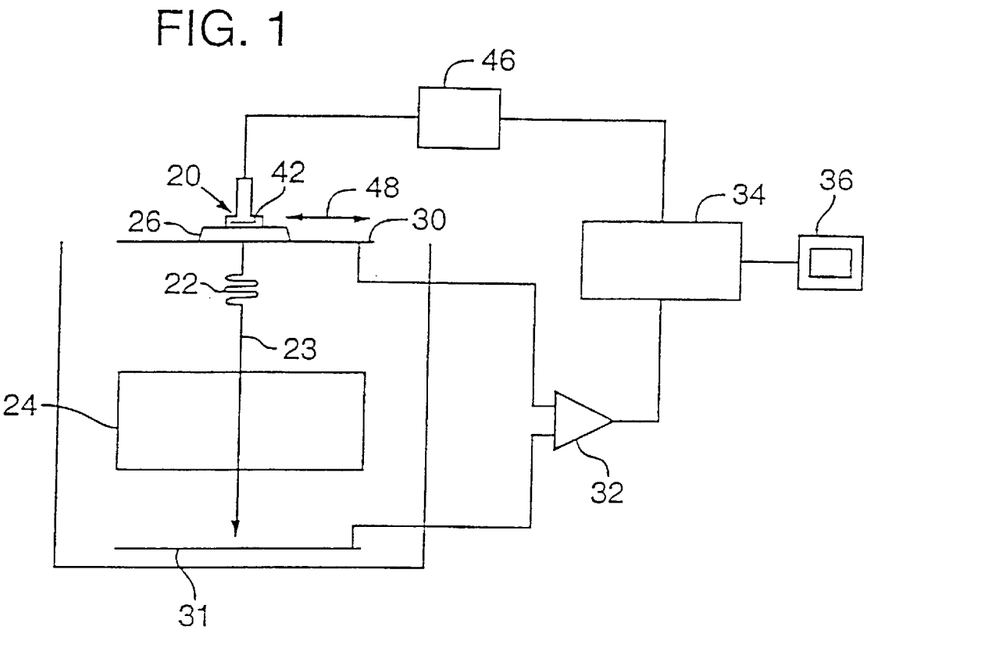
FIG. 1 is a schematic diagram of an electroacoustic imaging apparatus in which an acoustic wave is applied to a specimen.

With reference to FIG. 1, an apparatus for forward electroacoustic imaging comprises an acoustic transmitter 20 that generates an acoustic wave 22 that is coupled to a specimen 24 through an acoustic coupling medium 26, typically water or a water soluble gel. The acoustic wave 22 propagating in the specimen 24 produces an electric field that is detected as a voltage at electrodes 30, 31 that are in communication with an amplifier 32. The amplifier 32 delivers an amplified voltage signal at an output to a signal processor 34. The signal processor 34 receives the amplified voltage signal and generates an image that is displayed on a display 36. The acoustic transmitter 20 includes an acoustic transducer 42 made of a piezoelectric ceramic or polymer, or a crystalline piezoelectric material such as quartz. The acoustic transmitter 20 is connected to a transducer driver 46 that supplies a time varying voltage or voltage pulse to the acoustic transducer 42.

The acoustic wave 22 propagates as a longitudinal acoustic wave in the specimen 24 in a propagation direction 23. Therefore, the displacements of electrical charges produced by the electroacoustic effect are parallel to the propagation direction 23 and these displacements produce electric fields that are, for example, detected along the propagation direction 23. The acoustic transmitter 20 is situated so that the electrode 30 transmits the acoustic wave 22 to the specimen 24. To encourage transmission of the acoustic wave 22 by the electrode 30, the electrode 30 may be made of a thin metal foil.

To image the specimen 24, the transducer driver 46 applies a voltage pulse to the acoustic transducer 42, generating the acoustic wave 22. As the acoustic wave 22 propagates through the specimen 24, a voltage dependent on the local electroacoustic parameter $C_{ea}(r)$ appears across the electrodes 30, 31. Because the electroacoustically induced voltage propagates through the specimen 24 at a speed proportional to the speed of light in the specimen 24, the induced voltage corresponding to a selected specimen location appears across the electrodes 30, 31 approximately simultaneously with the propagation of the acoustic pulse through the selected specimen location. Because of the approximately simultaneous excitation of the electroacoustically induced voltage and the appearance of this voltage at the electrodes 30, 31, the magnitude and phase of the induced voltage associated with a specific specimen location is obtained by measuring the induced voltage as a function of a delay from the time at which the acoustic wave 22 is transmitted by the acoustic transmitter 20. The image processor 34 records the induced voltage as a function of the propagation time of the acoustic wave 22 through the specimen 24. Using the speed of sound in the specimen 24, the induced voltage as a function of the time elapsed from the generation of the acoustic wave 22 can be transformed into a function of specimen location. An exemplary induced voltage is depicted in FIG. 2 as a function of both the elapsed time and the specimen location.

Image resolution along the propagation direction 23 ("longitudinal resolution") is approximately equal to the product of the speed of sound and the duration of the acoustic wave 22, which is approximately equal to the duration of the voltage pulse from the transducer driver 46. For an acoustic wave having a 0.5 μs duration and a speed of sound in the specimen 24 of 1450 m/s (the speed of sound in water), the longitudinal resolution is about 0.7 mm. Acoustic waves of shorter duration are generally associated with higher resolutions but exhibit less optimal signal-to-noise ratio.

Figure 2:
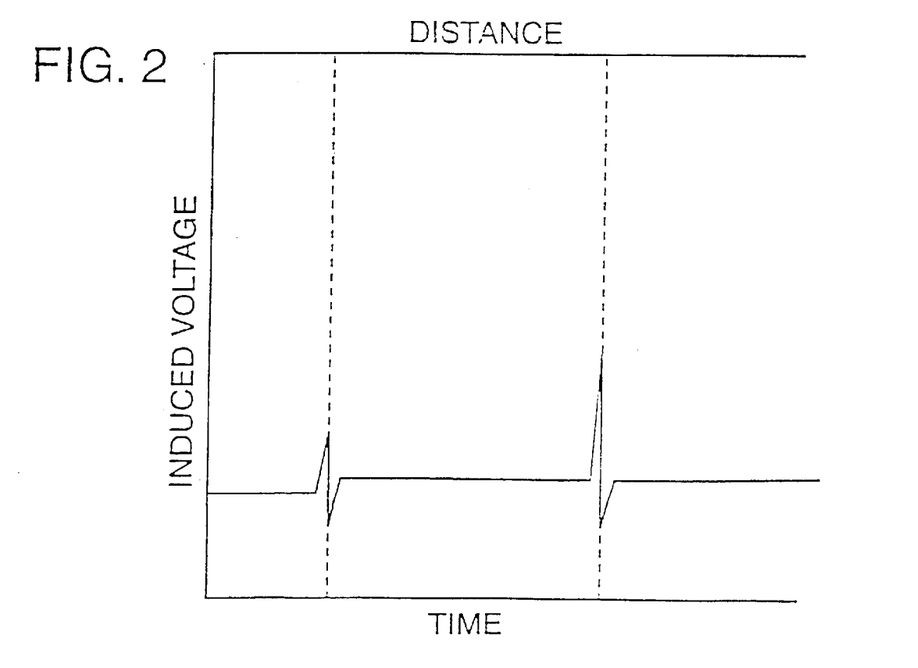
FIG. 2 is a graph of an electroacoustically induced voltage produced by an acoustic wave as a function of both delay from the application of the acoustic wave and specimen location.

The induced voltage shown in FIG. 2 provides a one-dimensional image of the specimen 24 along the propagation direction 23, i.e., an image dependent on $C_{ea}(r)$ along the propagation axis 23. To obtain a two-dimensional image, the acoustic transmitter 20 is incrementally moved along an axis 48 (which is substantially perpendicular to the axis 23 in FIG. 1). An acoustic wave similar to the acoustic wave 22 is directed into the specimen 24 and an induced voltage is recorded as a function of delay. This procedure is carried out repeatedly and the recorded induced voltages are combined to form a two-dimensional image. To obtain three dimensional images, the acoustic transmitter 20 is incrementally moved along the axis 48 in a different plane, for example a plane perpendicular to the axes 23, 48, and the induced voltages recorded and combined.

Image resolution in directions perpendicular to the propagation direction 23 ("transverse resolution") depends on the cross-sectional area of the region irradiated by the acoustic wave 22, and depends on the size and design of the acoustic transmitter 20. For example, a focused transducer produces an acoustic wave that converges to irradiate an area smaller than the emitting area of the focused transducer. Therefore, a focused transducer provides a greater transverse resolution than a conventional transducer having the same emitting area. Transverse resolutions of 0.1 mm, 1 mm, and 10 mm are typical. In general, longitudinal resolution is higher than transverse resolution.

The amplitude of the voltage pulse applied to the acoustic transmitter 20 is generally selected so that the acoustic wave 22 does not cause cavitation in the specimen 24. For imaging soft tissue, the approximate pressure at which cavitation begins is determined by (peak pressure)$^2$/(acoustic frequency)=0.5 Mpa$^2$/MHz. The amplitude of the acoustic wave 22 is then selected to be less than this value, for example less than about 50% or 20% of this value. The duration of the voltage pulse is selected to provide a predetermined longitudinal resolution, such as 0.1 mm, 0.5 mm, or 1.0 mm. Alternatively, the duration of the voltage pulse can be selected to obtain a predetermined signal-to-noise ratio, for example, 0.1:1, 1:1, or 10:1. Increasing the duration of the voltage pulse increases the total energy in the acoustic wave 22, leading to an improved signal-to-noise ratio. The signal-to-noise ratio can also be increased by averaging the induced voltages obtained with multiple repetitions of the voltage pulse, for example, by averaging 10, 100, or 1000 repetitions.

Figure 3:
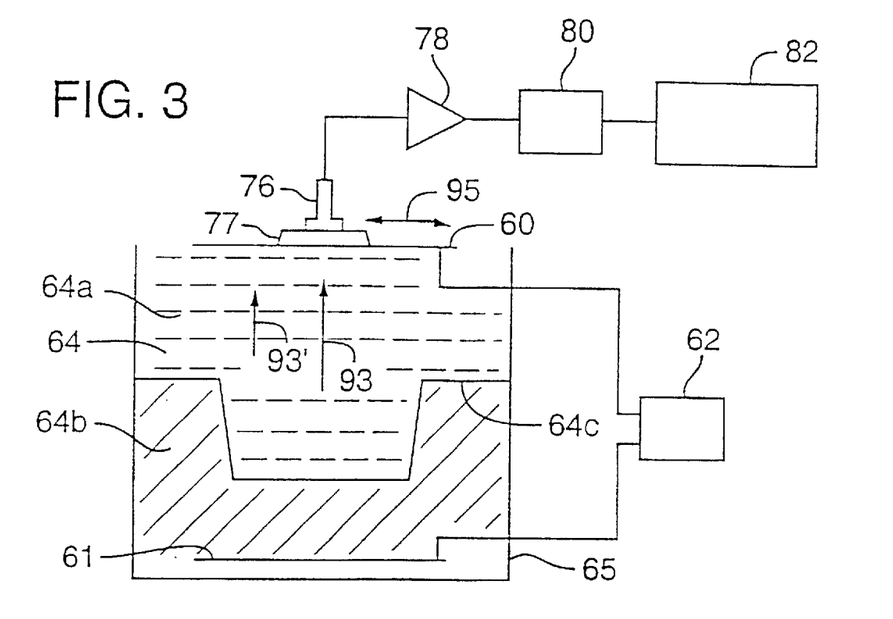
FIG. 3 is a schematic diagram of an electroacoustic imaging apparatus in which an electric field is applied to a specimen made of cooked eggwhite and saline solution.

With reference to FIG. 3, an apparatus for reverse electroacoustic imaging includes electrodes 60, 61 that receive an applied voltage from drive electronics 62 and apply a voltage to a specimen 64. The drive electronics 62 are adjustable to provide exponentially decaying pulses of peak voltage of 400 V and 300 ns full width at half maximum voltage. The applied voltage is plotted as a function of time in FIG. 4. The magnitude of the applied voltage may be limited to avoid dielectric breakdown or, in biological specimens, nerve stimulation. For example, voltages producing electric fields of magnitude at less than about 2000 V/m or 1000 V/m generally avoid these problems.

The specimen 64 is held in a cylindrical container 65 of diameter d=11.5 cm and height h=5.3 cm. A copper sheet secured to the bottom inner face of the container 65 with an adhesive layer serves as the electrode 61. A 15 μm thick sheet of aluminum foil that transmits the acoustic wave 22 to an acoustic receiver 76 serves as the electrode 60. The applied voltage produces an acoustic wave in the specimen 64 that is dependent on the local electroacoustic parameter $C_{ea}(r)$ of the specimen 64. The acoustic wave is received by an acoustic receiver 76 that converts the received acoustic wave into an electrical signal ("transduced signal") that is amplified by an amplifier 78. An image processor 80 receives the amplified transduced signal and forms an image that is displayed on a display 82.

Figure 5A:
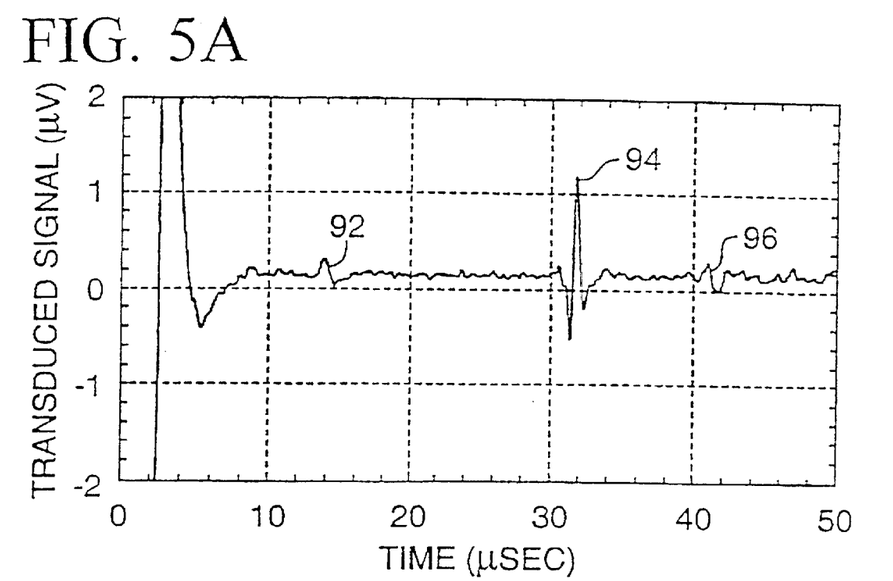
FIG. 5A contains a graph of transduced signal as a function of delay for the cooked eggwhite and saline solution specimen obtained with the apparatus of FIG. 3.

The specimen 64 includes a first layer 64a and a second layer 64b that are separated by an interface 64c. In a first example, the layer 64a is 0.25% saline solution and the layer 64b is cooked eggwhite. The layer 64a extends from an interface 64c with the layer 64b to the electrode 60. The acoustic receiver 76 is centered on the longitudinal axis of the container 65 and the electrode 60 is grounded. The transduced signal is shown in FIG. 5A. To reduce random noise in the transduced signal, the graph of FIG. 5A is an average of 1000 acquisitions of the transduced signal. Peaks 92, 94, 96 correspond to interfaces between the electrode 60 and the saline solution of the layer 64a, the saline solution of layer 64a and the cooked eggwhite of layer 64b, and the cooked eggwhite of layer 64b and the electrode 61, respectively. After reversing the polarity of the applied voltage so that the electrode 61 is grounded, the transduced signal of FIG. 5B results. The locations of the peaks 92, 94, 96 are unchanged, but the polarity (phase) of the peak 94 associated with the saline-eggwhite interface is reversed. This phase-reversal is due to the electroacoustic effect, and clearly identifies these transduced signals as dependent on the electroacoustic parameter $C_{ea}(r)$ instead of other possible mechanisms.

Figure 5B:
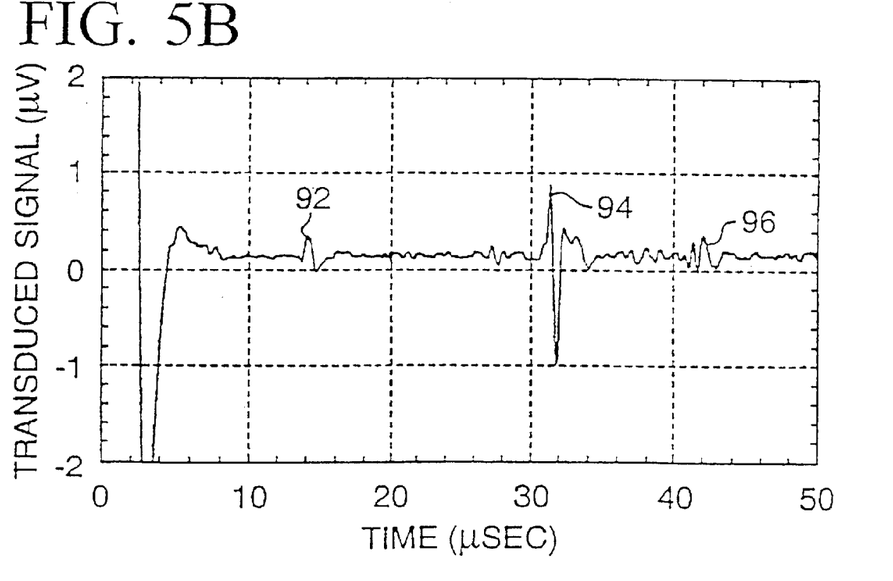
FIG. 5B contains a graph of transduced signal as a function of delay obtained with the apparatus of FIG. 3, but in which the cooked eggwhite and saline solution specimen has been replaced by an agarose and saline solution specimen.

The transduced signals of FIGS. 5A–5B correspond to an induced acoustic wave that propagates along an axis of propagation 93. To obtain a complete two-dimensional image, the acoustic receiver is incrementally moved parallel to an axis 95 and an induced acoustic wave is received along an axis 93'. This incremental movement and reception of induced acoustic waves along additional axes is repeated. The transduced signals corresponding to the acoustic waves received by these incremental movements are combined to form a two-dimensional image. The two-dimensional image (and the individual transduced signals that are combined to form the image) includes both an amplitude and a phase; either the amplitude, phase, or both can be used to display the image.

Figure 6A:
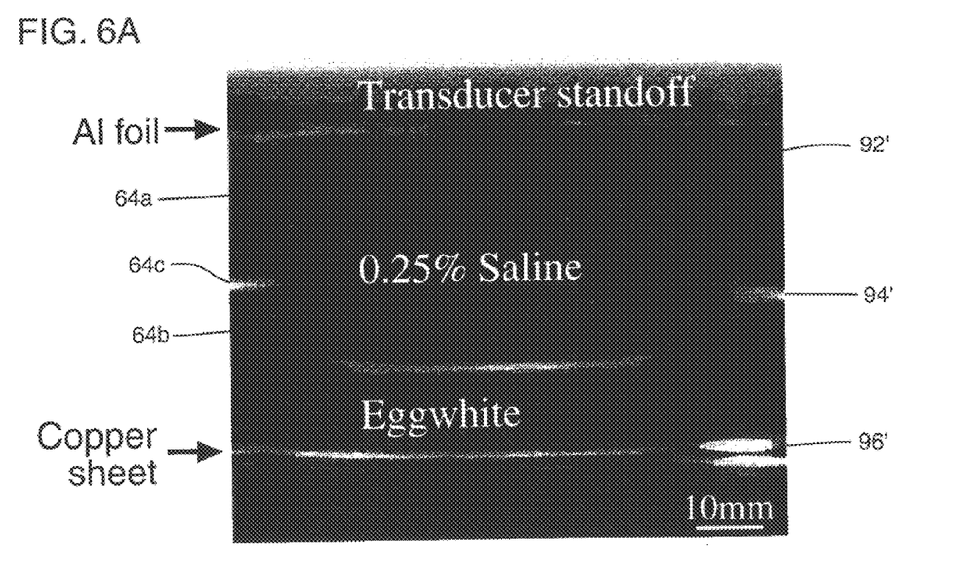
FIG. 6A is a two-dimensional image of the cooked eggwhite and saline solution specimen obtained with the apparatus of FIG. 3.

FIG. 6A contains an image of the first example specimen based on the amplitude of the transduced signals. The image is obtained by incrementally moving the acoustic receiver in 1.06 mm intervals parallel to the axis 95, and acquiring the transduced signals for each interval. Images can also be obtained using coarser or finer translation intervals, such as intervals in the ranges of 0.5–10 mm or 1–2 mm. In addition, if an array of acoustic receivers (or acoustic transducers) is provided, images can be obtained without incremental movement of the acoustic receiver 76.

Figure 6B:
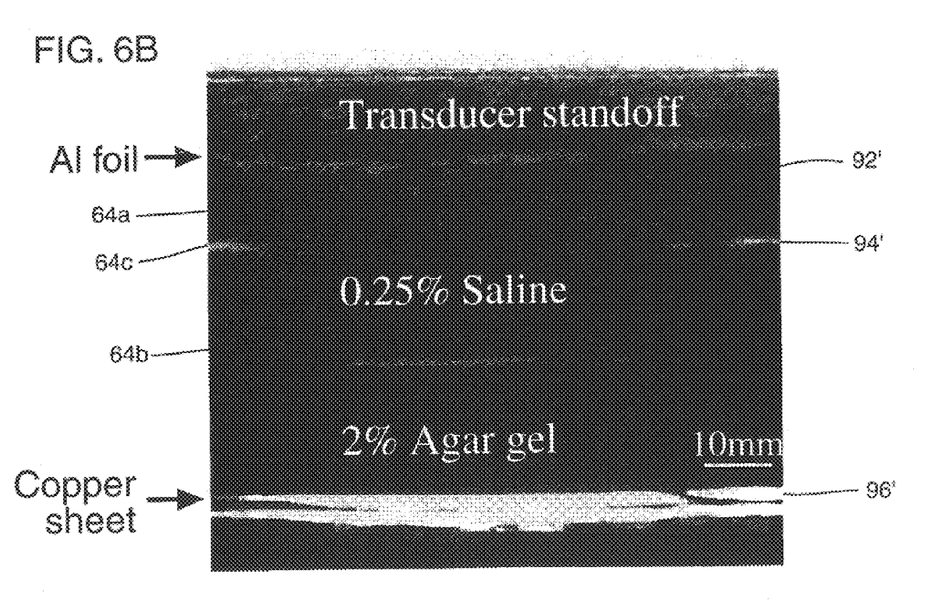
FIG. 6B is a two-dimensional image of the agarose and saline solution specimen obtained with the apparatus of FIG. 3

In a second example, the layer 64a is a 0.25% saline solution as in the first example, but the layer 64b is a 2% agarose solution (agar gel). The magnitude of the transduced signal is smaller for the second example specimen than for the first example specimen. Because the electroacoustic parameter $C_{ea}(r)$ of an ionic specimen is a function of the ion number density n and dynamic mobility m/η, the extensively cross-linked cooked eggwhite produces a larger transduced signal due to the large effective mass and low dynamic mobility of the cooked eggwhite. FIG. 6B contains a two-dimensional image of the second example specimen, similar to the image of FIG. 6A.

The transducer 77 is a so-called narrowband transducer that efficiently transduces acoustic waves only within a limited frequency range, for example 2.25 MHz ±0.25 MHz. In general, narrowband transducers are efficient at a center frequency $f_0$ and in a range $\pm \Delta f$ around $f_0$, where $\pm \Delta f/f_0$ is less than about 20%. With such a transducer, abrupt changes in the electroacoustic parameter $C_{ea}(r)$ appear distinctly in the transduced signal. Electroacoustically produced acoustic waves from regions in which $C_{ea}(r)$ is approximately constant are only weakly transduced. If broadband transducers are used (i.e., transducers that efficiently transduce a wide range of acoustic frequencies), electroacoustically produced acoustic waves from both discontinuities in $C_{ea}(r)$ and regions of constant $C_{ea}(r)$ appear distinctly in the transduced signal. The interfaces of the specimen 64 corresponding to the peaks 92, 94, 96 of FIGS. 5A–5B are marked as image interfaces 92', 94', 96' in FIGS. 6A–6B. The image interfaces 92', 94', 96' correspond to abrupt changes in the electroacoustic parameter $C_{ea}(r)$. Between the image interfaces 92', 94', 96', the electroacoustic parameter $C_{ea}(r)$ is nearly constant and the transduced signal is largely indistinguishable from random noise.

Figure 4:
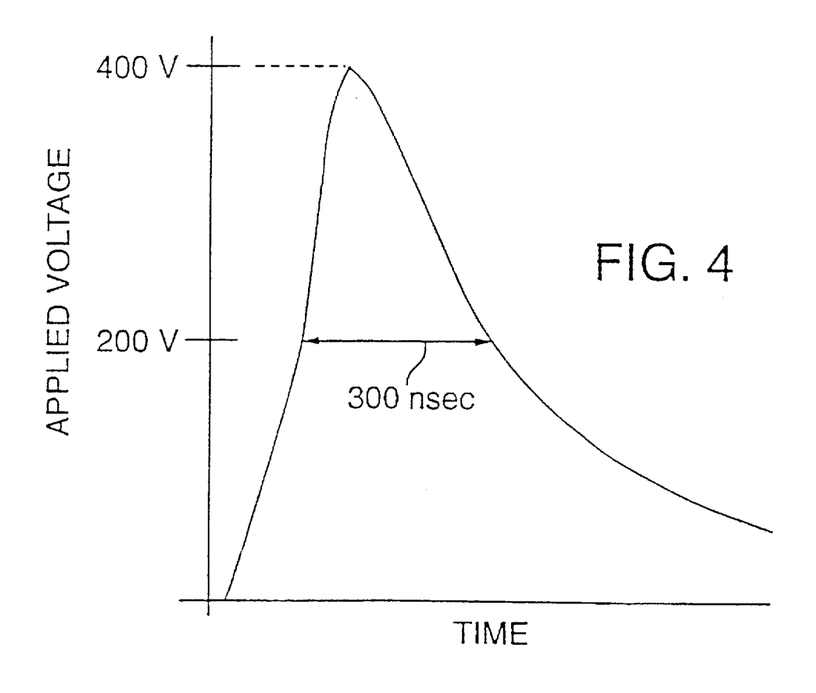
FIG. 4 contains a graph of an applied voltage as a function of time as used in the apparatus of FIG. 3.

The images of FIGS. 6A–6B are formed using the voltage pulse of FIG. 4 applied to the electrodes to obtain transduced signals similar to those of FIGS. 5A–5B. Such images are based on the time delay from the application of the voltage pulse to the arrival of acoustic waves at the acoustic receiver 76. Other imaging methods can be used as well. For example, a swept frequency voltage (i.e., a voltage with a time varying frequency) can be applied to the electrodes 60, 61 and the frequency of the transduced signal used to associate portions of the transduced signal with locations in the specimen 64. With a swept frequency voltage, longitudinal resolution depends primarily on the bandwidth of the frequency sweep and not on the duration of the voltage pulse. The total longitudinal distance imaged ("longitudinal field of view") is proportional to the frequency resolution of the sweep. For example, a 5 cm longitudinal field of view with a 1 MHz bandwidth frequency requires a 30 kHz frequency resolution and a rate of frequency sweep of about 1 MHz/ms or slower.

While the apparatus of FIG. 3 uses a piezoelectric transducer for detecting the induced acoustic wave and forming the transduced signal, other acoustic transducers can be used. Piezoelectric transducers not only detect acoustic waves but generate acoustic waves in response to an applied field. In the apparatus of FIG. 3, the application of the voltage pulse to the electrodes 60, 61 can produce an electric field at the acoustic receiver 76 despite the shielding effect of the electrode 60. An electric field at the electrode 60 causes the acoustic receiver 76 to generate an acoustic wave that can be reflected or scattered by the specimen 64 or the container 65 back to the acoustic receiver 76, contributing to the transduced signal but not indicative of the electroacoustic parameter $C_{ea}(r)$ of the specimen 64. Fiberoptic acoustic sensors detect acoustic waves using a fiber optic interferometer to sense a movement of an optical surface such as mirror caused by the acoustic wave. A piezoelectric transducer is not required so that unwanted acoustic waves are not piezoelectrically produced by the voltage pulse.

Figure 7A:
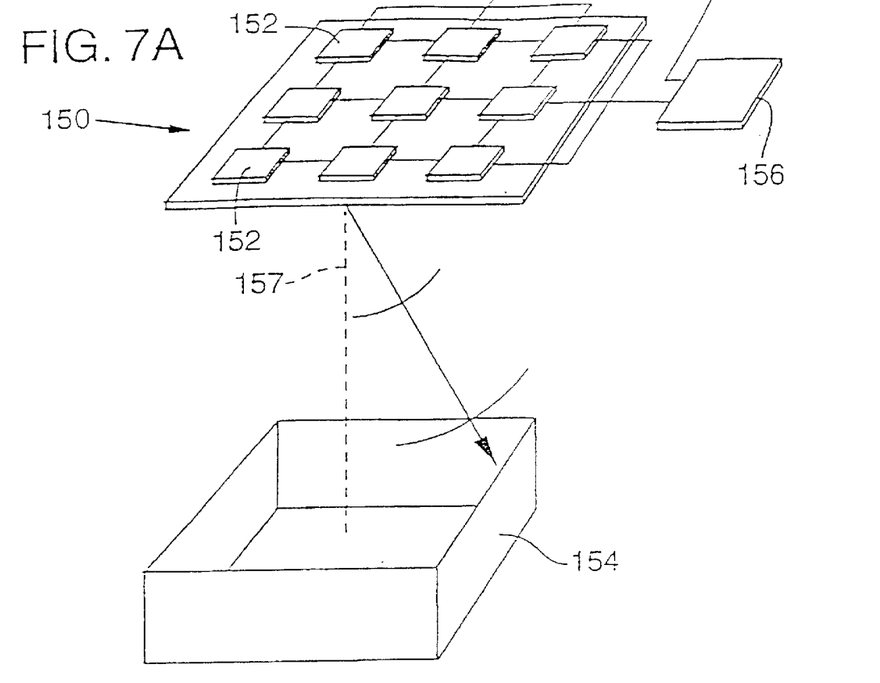
FIG. 7A is a schematic illustrating an array transducer that directs an acoustic wave into a specimen.

Transducer arrays can simplify image formation in forward or reverse electroacoustic imaging. With reference to FIG. 7A, an array 150 of transducers 152 is situated to direct an acoustic wave to a specimen 154 for forward electroacoustic imaging. An array driver 156 applies a voltage or series of voltages to the transducers 152. By adjusting the timing (or phase) of the voltages applied to the transducers 152, the acoustic wave produced is focused into the specimen 154 or steered with respect to a nominal direction of propagation 157. Alternatively, the acoustic wave can be both focused and steered. With such an array, the acoustic wave can be selectively directed to a location in the specimen, without moving the array 150.

Figure 7B:
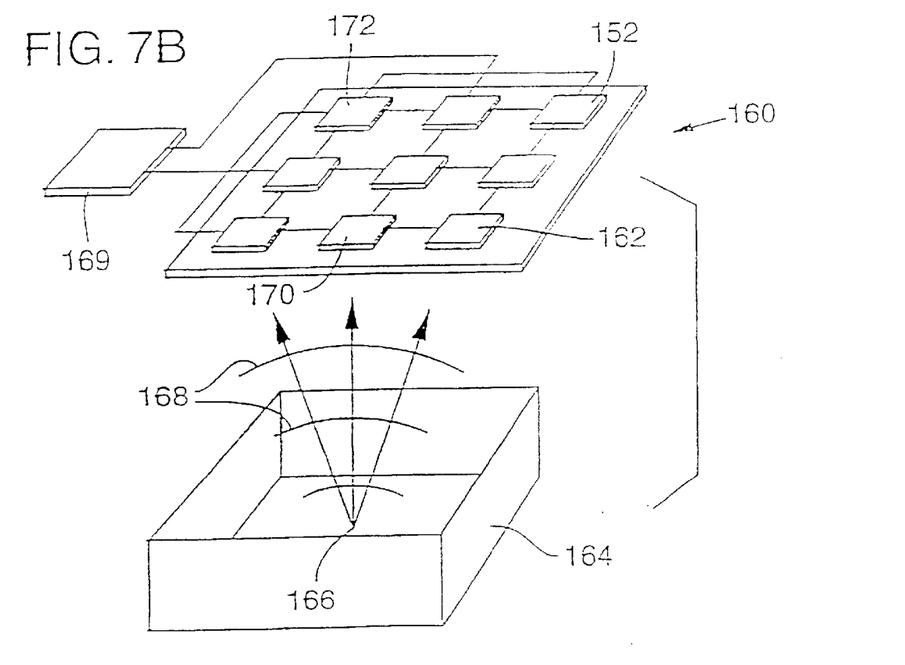
FIG. 7B is a schematic illustrating an array transducer that receives an induced acoustic wave from a specimen.

With reference to FIG. 7B, an array 160 of transducers 162 receives an induced acoustic wave produced by the reverse electroacoustic effect in a specimen 164 at a location 166. The propagation times for wavefronts 168 of the induced acoustic wave to propagate to a particular transducer of the array 160 depends on the distance of the transducer from the location 166. For example, the induced acoustic wave arrives at a transducer 170 before reaching a transducer 172 because the transducer 170 is closer to the location 166. By recording the amplitude and timing of the acoustic waves reaching the transducers of the array 160 with an image processor 169, the transduced signals from the array 160 can be associated with various locations in the specimen 164. This procedure is similar to triangulation or to methods used in so-called inverse source problems. Using the array 160, a two-dimensional image can be produced with a single application of a voltage to the specimen 164, and without movement of the array.

Some specimens have significant structures that can be inadvertently aligned so that an applied acoustic wave (forward electroacoustic imaging) propagates parallel to the interface. With such an alignment, the image interface is imaged with transverse resolution instead of the generally superior longitudinal resolution. To prevent this specimen alignment, acoustic waves can be applied along two or more non-parallel axes with corresponding pairs of electrodes to receive the induced voltages. With two or more non-parallel axes, specimen interfaces cannot be parallel to both axes. In reverse electroacoustic imaging, multiple electrode pairs can be provided with corresponding acoustic receivers so that an induced acoustic is received that does not propagate parallel to the specimen interface.

The application of an electric field to a specimen can produce an acoustic wave due to the thermoacoustic effect in addition to the electroacoustic effect. In addition, if a magnetic field is applied to the specimen, then the applied electric field can also produce an acoustic wave due to the Hall effect. Similarly, if an acoustic wave is applied to a specimen in a magnetic field, then an electric field is produced that can have contributions from both the Hall effect and the electroacoustic effect. Some images include contributions from more than one of these effects, i.e., electroacoustic, thermoacoustic, and Hall effects. For convenience, an image having a contribution from only one of these effects is referred to either as a purely electroacoustic, thermoacoustic, or Hall effect image.

As discussed above, the application of an acoustic wave to produce an electric field in a specimen, or the application of an electric field to produce an acoustic wave in a specimen, in the absence of heating and with no applied magnetic field, is referred to as the electroacoustic effect. In Hall effect imaging, an electric field is applied to a specimen in a direction perpendicular to the direction of an applied magnetic field. The electric field causes charged particles to move in a direction perpendicular to both the applied electric and magnetic fields due to the Lorentz force $F_L$, wherein $F_L$ is proportional to the magnitude and direction of the applied magnetic field and is perpendicular to both the applied electric and magnetic fields. This movement produces an acoustic wave, and an image can be obtained using the acoustic wave. The magnitude of the acoustic wave produced by the Hall effect is proportional to the applied magnetic field. The electroacoustic contribution to an image dominates the image in the substantial absence of a magnetic field on the specimen, defined as a condition in which the magnetic field experienced by the specimen has a magnitude such that a maximum Hall effect contribution to the image is less than, for example, about one-half, one-fourth, or one-tenth of a minimum electroacoustic contribution to the image.

To obtain the electroacoustic and the Hall effect images, an image $I_1$, is first obtained with an applied magnetic field B. Next, the direction of the applied magnetic field is reversed so that a magnetic field −B is applied, and an image $I_2$ is produced. The contribution of the electroacoustic effect to the images $I_1$, $I_2$ does not depend on the applied magnetic field B, and is unaffected by the sign change in the applied magnetic field B. In contrast, the contribution due to the Hall effect changes sign. The Hall effect and electroacoustic images can be extracted as $(I_1-I_2)/2$ and $(I_1+I_2)/2$, respectively. Alternatively, the applied magnetic field can be turned off, but a better image signal-to-noise ratio is obtained by reversing the sign of the applied magnetic field so that images such as $I_1$, $I_2$ are obtained.

More generally, changing the direction of the applied magnetic field permits a Hall effect image and a magnetic field independent image to be obtained. For example, if magnetic fields B and −αB are applied to obtain respective images $I_B$, $I_{\alpha B}$, the Hall effect image is proportional to $I_B-I_{\alpha B}$ and the magnetic field independent image is proportional to $\alpha I_B-I_{\alpha B}$.

The magnetic field independent image can be a mixed image with contributions from both the electroacoustic effect and the thermoacoustic effect. The thermoacoustic and electroacoustic contributions can be distinguished as well. A thermoacoustic image depends on specimen heating so that a thermoacoustic image is independent of the polarity of the applied voltage because voltages of either positive or negative polarity produce a temperature rise. In contrast, reversing the polarity of the applied voltage reverses the polarity of an electroacoustic image. If images $I_3$, $I_4$ are obtained (in the absence of a magnetic field) with voltages of different polarities but equal magnitudes, the thermoacoustic and electroacoustic images are proportional to $I_3+I_4$ and $I_3-I_4$, respectively. Applied voltages of other magnitudes and opposite polarities can also be used. If images $I_V$, $I_{\beta V}$ are obtained with applied voltages V, −βV, respectively, the thermoacoustic and electroacoustic images are proportional to $\beta I_V+I_{\beta V}$ and $I_V-I_{\beta V}$, respectively.

Therefore, an image containing contributions from the Hall effect, thermoacoustic effect, and electroacoustic effect can be analyzed to obtain purely Hall effect, thermoacoustic, and electroacoustic images. Because each of these images depends on different specimen properties or combinations of specimen properties, three different images are obtained.

Figure 8:
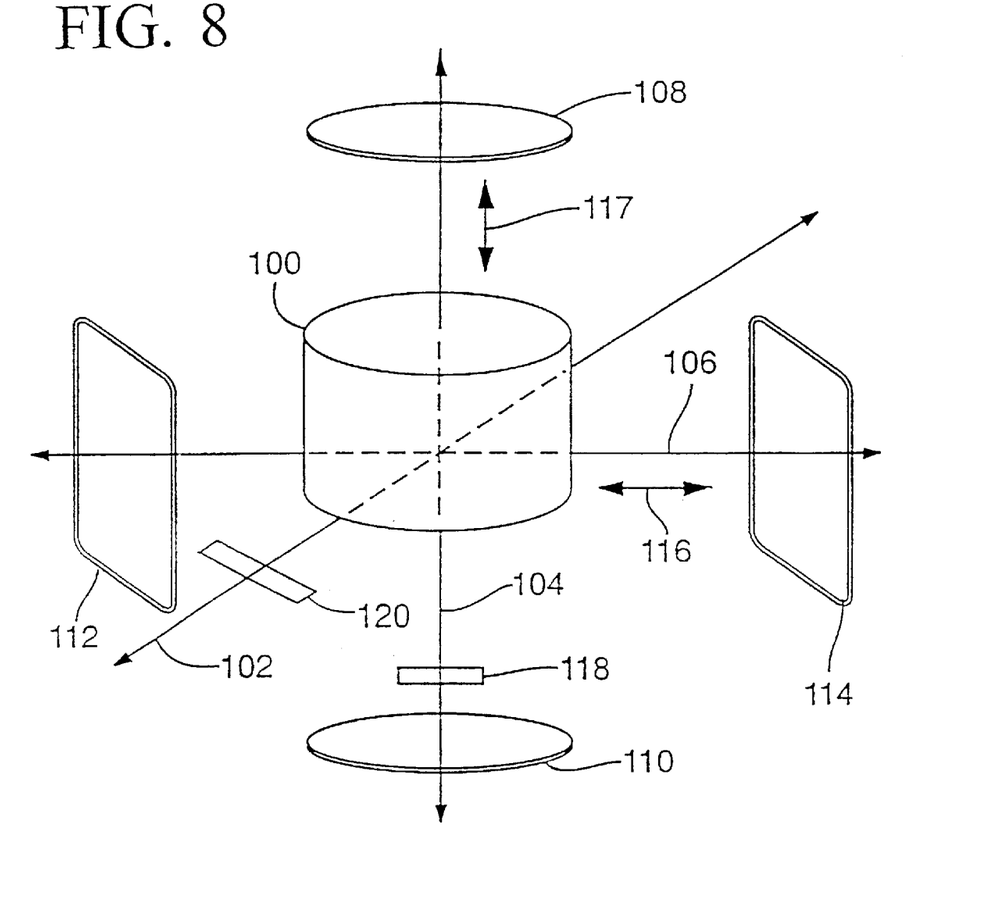
FIG. 8 is a schematic illustration of an arrangement of an electric field, a magnetic field, and acoustic receivers to distinguish acoustic waves generated by the electroacoustic and Hall effects.

An electroacoustic contribution to an image obtained in the presence of a magnetic field can also be distinguished from a Hall effect image by directional detection of the generated acoustic wave. In the Hall effect, the generated acoustic wave propagates in a direction perpendicular to the applied electric field and the applied magnetic field. The electroacoustically generated acoustic wave propagates parallel to the applied electric field. With reference to FIG. 8, a specimen 100 is shown with respect to orthogonal coordinate axes 102, 104, 106. Electrodes 108, 110 are situated along and perpendicular to the axis 104. Coils 112, 114 are arranged along the axis 106 and so that a current in the coils 112, 114 produces a magnetic field 116 parallel to the axis 106.

A voltage pulse is applied to the electrodes 108, 110, producing an electric field 117 parallel to the axis 104. The electric field 117 produces an electroacoustically generated acoustic wave that propagates parallel to the axis 104 and is received by a transducer 118. The acoustic wave generated by the Hall effect propagates parallel to the axis 102 in a direction perpendicular to both the electric field 117 and the magnetic field 116. A transducer 120 situated along the axis 102 receives the Hall effect acoustic wave. Transduced signals from the transducers 118, 120 are used to form an electroacoustic image and a Hall effect image of the specimen 100, respectively. Transducers situated at other locations with respect to the applied electric and magnetic fields produce transduced signals that include contributions from both the electroacoustic and Hall effect. For convenience, axes are defined as substantially perpendicular if an angle between the axes is about 90°±20°. If the magnetic field 116 is parallel to an axis that is substantially perpendicular to an axis parallel to the electric field 117, purely electroacoustic images and Hall effect images can be obtained by placing transducers appropriately.

In forward electroacoustic imaging, an applied electric field generates an acoustic wave that propagates parallel to the direction of the applied electric field. In contrast, the acoustic wave generated by the Hall effect propagates in a direction perpendicular to the applied electric field (and the magnetic field). Therefore, even with a magnetic field applied to a specimen, electroacoustic and Hall effect contributions can be distinguished by locating an acoustic receiver either parallel or perpendicular to the applied electric field. Using more than one acoustic receiver appropriately situated, both electroacoustic and Hall effect images can be obtained simultaneously.

A thermoacoustic contribution can also be distinguished from an electroacoustic contribution by changing the magnitude of the applied voltage. Specimen heating is proportional to the square of the applied voltage so that if images $I_5$, $I_6$ are obtained with applied voltages of magnitude V, γV, respectively, the electroacoustic and thermoacoustic contributions are proportional to $\gamma^2 V I_5-I_6$ and $\gamma I_5-I_6$, respectively.

For some specimens, the acoustic wave induced by the electroacoustic effect is much larger than the acoustic wave induced by the Hall effect unless the applied magnetic field is large. For example, in an extensively cross-linked material such as cooked eggwhite, 2.5 T applied magnetic field is required for the Hall effect acoustic wave to be of the same magnitude as the electroacoustically induced acoustic wave. In other specimens, an applied field of 2.5 T produces an acoustic wave via the Hall effect that is larger than the electroacoustically induced acoustic wave. For example, in a dilute material such as an agarose gel, the electroacoustically induced acoustic wave is 10–20 dB less than that produced by the Hall effect with an applied magnetic field of about 2.5 T.

Embodiments of the invention are disclosed in which electrodes are used to apply or detect electric field or voltages. Other voltage or electric field sensing elements such as coils can be substituted. Embodiments of the invention are described with reference to longitudinal acoustic waves. In many biological specimens, shear acoustic waves are rapidly attenuated, so that longitudinal acoustic waves are more optimal. In other specimens, such as semiconductor materials (e.g., silicon, gallium arsenide, germanium), shear waves are not rapidly attenuated. In such materials, electroacoustic imaging with shear waves is less problematic.

Whereas the invention has been described in connection with preferred embodiments, it will be understood that the invention is not limited to those aembodiments. On the contrary, the invention is intended to encompass all alternatives, modifications, and equivalents as may be included within the spirit and scope of the invention as defined by the appended claims.

We claim:

1. A method for producing an electroacoustic image of a specimen, comprising:

applying an electroacoustic probe signal to the specimen in the substantial absence of a magnetic field;

detecting an induced signal that is a function of an electroacoustic parameter of the specimen; and generating an image based on the detected induced signal.

2. The method of claim 1, wherein the electroacoustic probe signal is an acoustic wave and the induced signal is an electric field.

3. The method of claim 2, wherein the acoustic wave is applied so as to propagate along an axis of propagation and the electric field is detected along an axis that is substantially parallel to the axis of propagation.

4. The method of claim 1, wherein the electroacoustic probe signal is an electric field and the induced signal is an acoustic wave.

5. The method of claim 4, wherein the electric field is applied parallel to an axis and the acoustic wave is detected in a direction parallel to the axis.

6. The method of claim 1, further comprising applying a magnetic field to the specimen, wherein the induced signal is a function of the applied magnetic field and includes an electroacoustic contribution and a Hall effect contribution.

7. The method of claim 6, wherein the electroacoustic probe signal is an acoustic wave and the induced signal is an electric field.

8. The method of claim 6, wherein the electroacoustic probe signal is an electric field and the induced signal is an acoustic wave.

9. The method of claim 1, wherein the specimen is a biological specimen.

10. The method of claim 1, wherein the specimen is a human body.

11. The method of claim 1, wherein the specimen is a human bodily organ.

12. The method of claim 1, wherein the specimen is a human heart.

13. The method of claim 1, wherein the specimen is a tumor.

14. The method of claim 1, wherein the electroacoustic probe signal is applied along a plurality of incrementally displaced and substantially parallel axes.

15. A method for obtaining an image of a specimen, comprising:

applying a first magnetic field in a first direction to a specimen;

obtaining a first image of the specimen, the first image including electroacoustic and Hall effect contributions;

applying a second magnetic field to the specimen the second magnetic field in a direction opposite the first direction;

obtaining a second image of the specimen, the second image including electroacoustic and Hall effect contributions; and obtaining an electroacoustic image by combining the first and second images to substantially eliminate the Hall effect contribution.

16. The method of claim 15, wherein the first image and the second image include a thermoacoustic contribution.

17. The method of claim 15, further comprising combining the first image and the second image to obtain a Hall effect image.

18. A method for obtaining an electroacoustic image of a specimen in the substantial absence of a magnetic field, comprising:

applying a first voltage to the specimen to obtain a first image, the first voltage having a first polarity;

applying a second voltage to the specimen to obtain a second image, the second voltage having a second polarity opposite the first polarity; and combining the first image and the second image to obtain a purely electroacoustic image.

19. The method of claim 18, further comprising combining the first image and the second image to obtain a purely thermoacoustic image.

20. An apparatus for electroacoustic imaging of a specimen, comprising:

an acoustic transducer that produces an acoustic wave in the specimen, the acoustic wave electroacoustically generating an electric field;

electrodes that generate a voltage in response to the electric field; and an image processor that receives the voltage from the electrodes and produces an image of the specimen.

21. The apparatus of claim 20, further comprising a display that displays the image of the specimen.

22. The apparatus of claim 20, wherein the acoustic wave has a duration of less than about 1000 ns.

23. An apparatus for forward or reverse electroacoustic imaging of a specimen, comprising:

an acoustic transducer situated to transmit an acoustic wave to the specimen or to receive an acoustic wave from the specimen;

two or more electrodes situated to apply a voltage to the specimen or to detect a voltage produced by the acoustic wave transmitted by the acoustic transducer; and an image processor that receives an electroacoustically generated voltage from the electrodes or an electroacoustically generated acoustic wave from the acoustic transducer and forms an image of the specimen.

* * * * *